United States Patent
Klarhoefer et al.

(10) Patent No.: US 10,641,856 B2
(45) Date of Patent: May 5, 2020

(54) METHOD AND MAGNETIC RESONANCE APPARATUS FOR DIFFERENT DEGREES OF EXCITATION OF TWO DIFFERENT NUCLEAR SPIN TYPES

(71) Applicant: Siemens Healthcare GmbH, Erlangen (DE)

(72) Inventors: Markus Klarhoefer, Loerrach (DE); Thorsten Feiweier, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 275 days.

(21) Appl. No.: 15/891,895

(22) Filed: Feb. 8, 2018

(65) Prior Publication Data
US 2018/0231630 A1    Aug. 16, 2018

(30) Foreign Application Priority Data
Feb. 10, 2017  (DE) .......................... 10 2017 202 145

(51) Int. Cl.
| | | |
|---|---|---|
| *G01R 33/56* | (2006.01) | |
| *G01R 33/32* | (2006.01) | |
| *G01R 33/48* | (2006.01) | |
| G01R 33/561 | (2006.01) | |
| A61B 5/055 | (2006.01) | |
| G01R 33/54 | (2006.01) | |

(52) U.S. Cl.
CPC ......... *G01R 33/5607* (2013.01); *G01R 33/32* (2013.01); *G01R 33/4828* (2013.01); *A61B 5/055* (2013.01); *G01R 33/546* (2013.01); *G01R 33/561* (2013.01)

(58) Field of Classification Search
CPC ............... G01R 33/32; G01R 33/4828; G01R 33/4833; G01R 33/4835; G01R 33/446; G01R 33/4607; G01R 33/561; G01R 33/546; G01R 33/6507; A61B 5/055
See application file for complete search history.

(56) References Cited

U.S. PATENT DOCUMENTS

| | | | |
|---|---|---|---|
| 5,557,202 A | 9/1996 | Miyazaki et al. | |
| 5,891,032 A * | 4/1999 | Harvey ................ | G01R 33/446 324/306 |
| 6,850,793 B1 * | 2/2005 | Miyazaki ............... | G01R 33/54 324/307 |

(Continued)

OTHER PUBLICATIONS

Hauger, et al.: "Water Excitation as an Alternative to Fat Saturation in MR imaging: Preliminary Results in Musculoskeletal Imaging"; Radiology; vol. 224, No. 3; pp. 657-663; (2002).

*Primary Examiner* — Son T Le
*Assistant Examiner* — Dustin R Dickinson
(74) *Attorney, Agent, or Firm* — Schiff Hardin LLP

(57) ABSTRACT

In a method and magnetic resonance (MR) apparatus for different degrees of excitation of two different nuclear spin types with Larmor frequencies that are shifted relative to one another during recording of MR data by execution of an MR sequence, an excitation pulse sequence with at least two consecutive excitation pulses with defined time intervals for the exclusive excitation of the first spin type, and an additional pulse sequence with at least one additional pulse that acts at least on the second spin type, are used. A total pulse sequence formed by superimposition of the two pulse sequences is emitted within an excitation period of the MR sequence.

18 Claims, 9 Drawing Sheets

(56) References Cited

U.S. PATENT DOCUMENTS

2002/0183614 A1    12/2002  Feiweier et al.
2010/0286802 A1    11/2010  Feiweier et al.
2015/0331076 A1*  11/2015  Neji .................. G01R 33/4835
                                                         324/309

\* cited by examiner

METHOD AND MAGNETIC RESONANCE APPARATUS FOR DIFFERENT DEGREES OF EXCITATION OF TWO DIFFERENT NUCLEAR SPIN TYPES

BACKGROUND OF THE INVENTION

Field of the Invention

The invention concerns a method for different degrees of excitation of two different nuclear spin types with Larmor frequencies that are shifted relative to one another during recording of magnetic resonance data, by operation of a magnetic resonance (MR) sequence in an MR scanner.

Description of the Prior Art

In magnetic resonance imaging, the examination object, frequently a patient, is introduced into a strong magnetic field, whereupon nuclear spins in the object are excited by an excitation pulse. During relaxation of this excitation, magnetic resonance signals are emitted that are detected as magnetic resonance data, which can be transferred into image data or spectroscopic data. Numerous imaging techniques are known and diagnostic issues exist for which certain spin types (spin species) and/or their signal contributions need to be suppressed, both in magnetic resonance imaging and magnetic resonance spectroscopy. For example, as a result of binding conditions, nuclei of hydrogen atoms (protons) respectively bound in fat and water molecules have different resonance frequencies (Larmor frequencies). The difference in the Larmor frequencies is called chemical shift. This chemical shift is characteristic of the two spin types (spins of fat-bound protons or spins of water-bound protons) and, for the majority of fat protons, is approximately 3.3 ppm, i.e. approximately 440 Hz at 3 tesla and approximately 220 Hz at 1.5 tesla.

In certain recording techniques, as complete as possible suppression of the content of certain spin types, for example the fat signal components, in the magnetic resonance images or magnetic resonance spectra is mandatory. Such recording techniques include, for example, echo-planar imaging (EPI), which has a very small pixel bandwidth along the phase-encoding direction, and therefore would depict the fat image components shifted by several pixels relative to the water image components.

Suppression of fat signal components (e.g. signal components or other spin types) can also be advantageous with other imaging methods, for example turbo-spin-echo imaging (TSE) or gradient-echo imaging. With such imaging types, the fat signal is generally shown very light, and hence can complicate the identification of small structures in the water signal components. However, complete suppression of the fat signal components, for example in the imaging of joints, can complicate anatomical orientation.

Several suppression techniques for certain spin types are known in the prior art, each with its own advantages and drawbacks.

A first of these techniques is called spectrally selective suppression, with which a dedicated, spectrally selective radio-frequency excitation pulse tips the longitudinal magnetization of the spin type to be suppressed into the transverse plane, where it is dephased by spoiler gradients (dephasing gradients). The flip angle can be adjusted in order to achieve partial suppression of the spin type, but it still supplies a signal. This has the drawback that the suppression requires an additional suppression pulse sequence, which requires additional time in the magnetic resonance sequence. A further drawback is that the excitation pulse acts globally, i.e. on the entire examination volume, and hence is unable to benefit from dynamic adjustment.

Dynamic adjustment is an image-quality enhancement technique used in recording processes for a number of recording volumes, for example a number of slices or a number of slabs. Dynamic adjustment has the object, for each recording volume, of optimizing recording parameters targeted to local optimization of the image quality in the current recording volume, with respect to the prevailing field homogeneity or inhomogeneity. Herein, recording parameters to be adjusted can relate to pulse parameters of excitation pulses of an excitation pulse sequence for the spin type to be recorded, for example the choice of center frequency. One example of dynamic adjustment is described in DE 10 2009 020 661 A1.

A further suppression technique known in the prior art is spectrally selective inversion (SPAIR). With this technique, a dedicated, spectrally selective radio-frequency inversion pulse inverts the longitudinal magnetization of the spin species to be suppressed, i.e. the spin type. Following a defined waiting time, which is determined by the zero crossing of the magnetization, which is relaxing with the relaxation time T1, of the spin type to be suppressed, the imaging starts with the then-prevailing longitudinal magnetization of the spin type to be measured. Advantageously, it is thereby possible to react more robustly to variations of the radio-frequency field (B1 field) than is the case of spectrally selective suppression. The adjustment of the waiting time after the inversion pulse enables partial suppression of the signals of the spin type to be suppressed. Disadvantageously, this once again requires a suppression pulse sequence with the inversion pulse, which, including the waiting time, results in additional measuring time. Moreover, the inversion pulse also acts globally on the entire examination volume, and hence is unable to benefit from dynamic adjustment.

Another technique is "short tau inversion recovery" (STIR), wherein a recording-volume-specific radio-frequency inversion pulse inverts the longitudinal magnetization of all spin types. Following a defined waiting time, which is determined by the zero crossing of the magnetization of the spin type to be suppressed, which once again relaxes with T1, the imaging starts with the then-prevailing longitudinal magnetization. This method is advantageously not very sensitive to basic field inhomogeneities (B0 inhomogeneities) and adjustment of the waiting time can achieve partial suppression. Disadvantageously, once again, together with the waiting time, the suppression pulse sequence requires additional measuring time and the inversion also causes the useful signal of the spin type that is not to be suppressed to be significantly reduced.

Also known in the prior art is the Dixon technique, with which the at least two images are recorded with different echo times and such that the spins of the first spin type, which are to be measured, and the spins of the second spin type, which are to be suppressed, have different relative phase angles. Dedicated image processing methods are used to calculate separate images of the two spin types therefrom. This method has the advantage that it reacts less sensitively to basic field inhomogeneities and also that the partial suppression of the unwanted spin type is subsequently freely adjustable (in this respect, see DE 101 19 784 B4). Disadvantageously, two image recordings with special restrictions are required, and errors in the image processing can result in transposition of the spin types in the individual images.

Finally, also known in the prior art is spectrally selective excitation (water excitation). In this case, a special, recording-volume-specific excitation pulse sequence is used that excites only the spins of the spin type that is not to be suppressed. This exploits the fact that, once excited, with a chemical shift, spins demonstrate a different chronological phase evolution. Once again, this means that excitation pulses radiated at later times have different effects on the different spin types. If the times at which the different excitation pulses of the excitation pulse sequence are radiated and their degrees of excitation (flip angles) are suitably chosen, it is possible to again achieve longitudinal orientation of the spins of the spin type to be suppressed at the end of the excitation pulse sequence, i.e. in the direction of the basic field (effective flip angle=0), while the spins of the spin type to be recorded are deflected by a desired flip angle, i.e. excited.

Typically, binomial pulse sequences (or binomial pulses for short) are used with spectrally selective excitation. This means excitation pulse sequences composed of multiple excitation pulses with periodic "pass bands" and "stop bands" in the frequency domain, in which a spectral pass band is applied to the frequency of the spin type to be recorded (for example water spins) and a spectral stop band to the frequency of the spin type to be suppressed (fat spins). Binomial pulses are families of combined excitation pulses with a relative flip angle ratio corresponding to the binomial coefficient, for example 1-1, 1-2-1, 1-3-3-1, 1-4-6-4-1, etc. In each case, there is an evolution time T between two of these individual excitation pulses, in which time ideally a relative phase angle of 180° ($\pi$) develops between the spins of the first spin type, to be recorded, and those of the second spin type, to be suppressed. When considering water and fat protons with a field strength of 3 tesla, T is approximately $\pi/(2\pi*440 \text{ Hz})=1.1$ ms. Variants n with shorter evolution times in which a relative phase angle of, for example, only 90° ($\pi/2$) develops are known in the prior art.

As an example, reference is made to spectrally selective excitation, specifically in the context of water excitation, as described in the article by O. Hauger et al., "Water Excitation as an Alternative to Fat Saturation in MR Imaging: Preliminary Results in Musculoskeletal Imaging", Radiology 2002 (224), pages 657-663.

The special advantage of spectrally selective excitation is that it enables a time-saving procedure or the use of additional suppression pulse sequences. Disadvantageously, partial suppression of unwanted spin types is not possible.

SUMMARY OF THE INVENTION

An object of the invention is to expand the use of spectrally selective excitation.

This object is achieved by a method of the type described above wherein, in accordance with the invention, an excitation pulse sequence is used that has at least two consecutive excitation pulses with defined time intervals for the exclusive excitation of the first spin type, and an additional pulse sequence is also used that has at least one additional pulse that acts at least on the second spin type. A total pulse sequence formed by superimposition of the two pulse sequences is emitted within an excitation period of the magnetic resonance sequence.

Herein, the first spin type (to be measured) is significantly excited to a greater degree than the second spin type. Therefore, the basic concept of the invention is the superimposition, in a computer, of a number of excitation modules or pulse sequences and the use of the resulting cumulative coherence for the imaging. Based on a spectrally selective excitation pulse sequence known from the prior art, a second excitation module—the additional pulse sequence—is added in a suitable way within the excitation period. This takes place preferably by pulse superimposition, so that the desired effect is achieved, which is the excitation of the first spin type and the additional partial excitation of the second spin type. Therefore, the excitation pulse sequence involves spectrally selective excitation that is known in principle. Thus, the excitation pulse sequence exploits the different chronological development, in particular phase shift, of the spin types with respect to one another, by a selective choice of output times and degrees of excitation of the excitation pulses. This causes the excitation contributions at the Larmor frequency of the second spin type to be mutually compensatory, so that it is only when using the excitation pulse sequence there would be no excitation of the second spin type. However, the additional pulse, which acts at least on the second spin type, enables such a (lesser) excitation of the second spin type.

In this way, the present invention enables a combination of the advantages of spectrally selective excitation (fast method without the need for additional suppression modules) with the possibility of a defined, only partial suppression of a second spin type. This facilitates, for example in orthopedic imaging, anatomical orientation and results, particularly in combination with dynamic adjustment, with a simultaneously improved homogeneity of the desired contrast.

The MR data acquired with the total pulse sequence are compiled by the computer in a memory as a data file, and the data file is made available from the computer as an electronic signal.

In the case of the excitation pulse sequence, it is preferable to use a binomial pulse sequence as the excitation pulse sequence and/or the additional pulse sequence, as is known in principle from the prior art and was described in detail above. However, the method according to the invention is not restricted to binomial pulse sequences, but is generally applicable with spectrally selective excitation pulses.

Although the following description uses the example of spins of water-bound protons as the first spin type and spins of fat-bound protons as the second spin type, the present invention can be applied to all combinations of spin types to be suppressed and to be measured. For example, it is applicable also for fat imaging with water suppression or with respect to other combinations, for example spins of water protons as the first spin type and spins of protons bound in silicone as the second spin type. Particularly when using binomial pulse sequences, the known periodicity of the spectral excitation pattern can be used to predict the excitation intensity of further spin types. Adjustment of the interval between excitation pulses can be used to change the period in the frequency space, adjustment of the amplitude of the additional pulses according to the invention can be used to change the excitation amplitude.

The present invention can be used particularly advantageously when a turbo-spin-echo sequence (TSE sequence) is used as the magnetic resonance sequence. The method according to the invention then enables turbo-spin-echo imaging with an in particular adjustable degree of fat signal reduction in conjunction with optimum exploitation of the advantages of dynamic adjustment; this will be dealt with in more detail in the following.

Within the context of the method according to the invention, it is preferable for the pulse sequences to be emitted at least partially superimposed. In particular, a chronologically shorter pulse sequence is completely contained within the duration of the chronologically longer pulse sequence so that it is possible to achieve the shortest possible excitation period. However, it is also conceivable for at least one of the at least one additional pulse to be output after the end of the excitation pulse sequence. This means that it is not generally necessary for the superimposed additional pulse sequence to be applied synchronously with the excitation pulses of the spectrally selective excitation pulse sequence or in the same time window, but the at least one additional pulse can be played out in advance, or preferably afterward. Herein, the interval between the at least one additional pulse and the spectrally selective excitation pulses is irrelevant for the spectrum of the total pulse sequence.

Preferably, the at least one additional pulse is applied within the spectrally selective excitation module, i.e. the spectrally selective excitation pulse sequence, in order not to have to prolong the overall duration of excitation, i.e. the excitation period.

It is preferable for at least one additional pulse to be superimposed synchronously with an excitation pulse. Then, finally, the superimposition of the additional pulse and the excitation pulse can be emitted as a modified result pulse so that it is also not necessary to increase the pulse number in the excitation period. In an embodiment of the present invention, at least one additional pulse of the additional pulse sequence is selected such that an excitation pulse present at the start or end of the excitation pulse sequence is compensated, wherein the duration of the excitation period is selected as shorter than the duration of the excitation pulse sequence. In such a case, in which the additional pulse sequence includes an excitation pulse compensating an excitation pulse present at the start or end of the excitation pulse sequence, finally one of the excitation pulses is lost as a result of the superimposition, thus shortening the excitation pulse sequence, and enabling a reduction of the excitation period.

If, for example, a 1-2-1-binomial pulse sequence is used as an excitation pulse sequence, generally superimposition with the additional pulse sequence can result overall, for example, in a 1-2-x pulse sequence. Although it is possible to select x=0.5, it is preferable to design the additional pulse such that x=0 results, and hence shorter overall pulse sequences result compared to the prior art.

It should be noted with such embodiments, but also generally, that when the additional pulse sequence also acts on the spins of the first spin type it may be necessary to adjust the excitation pulse sequence in order to obtain the desired resulting flip angle for the first spin type. For the example just cited, when a 1-2-0 pulse sequence results and the excitation pulses supply $\alpha'/4$, $\alpha'/2$ and $\alpha'/4$ to the flip-angle contribution, and the one additional pulse provided synchronously to the last excitation pulse supplies $-\alpha'/4$ to the flip-angle contribution, when a flip angle $\alpha$ is to be achieved for the first spin type, $\alpha'=4/3\ \alpha$ should be selected, for example.

In the sense of superimposition, it is also possible to not provide the additional pulse synchronicity, but, for example, to radiate the additional pulse between two excitation pulses. For example, with a 1-2-1-binomial pulse sequence, an additional pulse is radiated exactly between the second and third excitation pulses. In the case of non-centered superimposition (the pulse centroid of the additional pulse sequence does not correspond to the pulse centroid of the excitation pulse sequence), it is no longer possible to uniquely define the starting time point that is relevant for the evolution of the transverse magnetization, so that the effective echo time (TE) for the spin types can differ slightly. For some imaging methods, such as gradient echo imaging, this may not have any significant negative effects or may even be desirable, such as for setting a defined phase angle for the magnetization of the different spin types. With other methods, however, discrepant signal evolutions of different spin types, such as turbo-spin-echo imaging, can result in unwanted interference in different signal paths. For this reason, as long as the method according to the invention is to be used in a sensitive magnetic resonance sequence of this kind, centered superimposition of the excitation pulse sequence and the additional pulse sequence is particularly preferable. This results in an advantageous embodiment wherein an (preferably binomial) excitation pulse sequence with an uneven number of excitation pulses is used, and an additional pulse sequence with one single additional pulse is used, which is superimposed synchronously with the central excitation pulse of the excitation pulse sequence. Therefore, if once again a 1-2-1-binomial pulse sequence is considered as an excitation pulse sequence, the superimposition preferably results in a 1-(2+x)-1 pulse sequence, for example a 1-3-1-total pulse sequence.

Within the context of the present invention, however, it is not necessary for the additional pulse sequence to include only one single additional pulse. More than two additional pulses of the additional pulse sequence may be present. In this context, in an embodiment the additional pulse sequence includes at least two consecutive additional pulses with defined time intervals for the exclusive excitation of the second spin type, wherein the flip angle achieved by the additional pulse sequence is smaller than the flip angle achieved by the excitation pulse sequence. Therefore, in this case, the additional pulse sequence also represents a spectrally selective excitation, but for the second spin type and of a lesser degree than the spectrally selective excitation of the first spin type by the excitation pulse sequence. This has the advantage that the excitation pulse sequence does not have to be modified with respect to the desired flip angle while additional excitation of the second spin type can nevertheless be provided.

In this context, it is advantageous for the excitation pulse sequence and the additional pulse sequence to be structurally the same, i.e. to have the same pulse number, the same pulse shape and the same time intervals, so that an excitation pulse and an additional pulse are always provided synchronously, which can result in modified result pulses of the total pulse sequence. For example, binomial suppression pulse sequences, i.e. off-resonant excitation pulse sequences, are known with which the phase of each second excitation pulse is inverted. For example, a 1-2-1 water excitation pulse sequence becomes a 1-2-1 fat excitation pulse sequence, a 1-3-3-1 water excitation pulse sequence becomes a 1-3-3-1 fat excitation pulse sequence etc. Thus, a combination of a spectrally selective excitation with the flip angle $\alpha$ for the first spin type with a spectrally selective excitation with the flip angle $\beta$ for the second spin type again produces the desired result as a superimposition. If, for example, a 1-2-1-flip angle $\alpha$-excitation pulse sequence is superimposed with a 1-2-1-$\beta$-additional pulse sequence, wherein $\beta=\alpha/8$, the resulting superimposition is a pulse sequence of the type ⅞-18/8-⅞. As is also generally the case, it is also conceivable to freely select the relative phase angle of the respective pulses to be superimposed as a result of which the phase of the resulting signal components is different. Usually, preference should be given to in-phase signal components due to the smoother spectral profiles. However, also conceivable are individual cases in which other phase relationships may be desirable, for example, in which the phase of the signal of the first spin type is opposite to the phase of the signal of the other spin type. In principle, superimpositions of different orders of binomial pulse sequences are also possible (for example, 1-3-3-1 excitation pulse sequences combined with a 1-1 additional pulse sequence).

As already indicated, it is conceivable, for the at least one additional pulse to be output with a relative phase to the excitation pulses. The choice of the relative phase of the superimposed additional pulse can exert an influence on the shape of the excitation spectrum and the degree of suppression of the second spin type.

In another embodiment of the invention, the above statements are transferred to spatially and spectrally selective excitation pulse sequences. Spatially-selective excitation pulse sequences permit the spectrally selective excitation of individual recording volumes, in particular individual slices or recording volumes that are to be recorded three-dimensionally ("slabs"). Therefore, the excitation pulse sequence and the additional pulse sequence can be emitted spatially selectively by the application of an assigned gradient pulse sequence. Therefore, the spatial selectivity is achieved by the application of a slice selection gradient pulse parallel to each excitation pulse (or additional pulse), wherein furthermore suitable excitation pulse shapes and additional pulse shapes, are to be used. For example, sinc pulses and/or Gaussian pulses and/or sinusoidal half waves can be used as pulses of the pulse sequences. Herein, it is possible to use different types of gradient pulse sequences, wherein the gradient pulse sequence should be selected such that, after the end of the excitation period, the effective gradient moment for the pulse sequences is identical, i.e. the gradient moments are applied in a suitably balanced form. Furthermore, the gradient pulse sequences frequently also have a last rephasing gradient pulse that is used for moment rephasing. Alternating slice selection gradients or a flyback technique can be applied in the gradient pulse sequence. Flyback techniques use additional gradient pulses for rephasing in order to enable the same gradient +/− sign with all gradient pulses output for excitation pulses and additional pulses. This ensures that local field inhomogeneities have the same effect with each excitation pulse, in particular with respect to the shape and location of the excited slice.

In the case of spatially selective pulse sequences, it is advantageous to make adjustments of recording parameters specific for the recording volume, in particular shim parameters and/or pulse parameters, for example the center frequency. Such adjustments are called dynamic adjustment, as described in DE 10 2009 020 661 A1 noted above. While spectral suppression techniques with additional suppression pulse sequences usually have a global effect, and therefore do not obtain any advantage from dynamic adjustment, spatially spectrally selective excitation techniques, such as water excitation, benefit significantly from local optimization of shim parameters and pulse parameters because more homogeneous excitation of the first spin type and more homogeneous partial excitation of the second spin type are achieved. For example, more homogeneous water excitation and more homogeneous fat excitation can be achieved simultaneously in order to permit improved anatomical orientation. This is particularly advantageous if a number of recording volumes, for example a number of slices, are to be acquired in succession.

Therefore, at least one pulse parameter of the pulses, which is emitted in a spatially selective manner (i.e. the excitation pulses and the additional pulses) and/or at least one shim parameter of a shim device of the magnetic resonance scanner, can be adjusted to the spatially selected recording volume in a dynamic adjustment. Specifically, it is possible for the center frequency to be dynamically adjusted as this pulse parameter.

In another embodiment of the invention, the relative degree of excitation of the two spin types is selected as a function of a user input. Therefore, by entering a corresponding recording parameter, the degree of the additional partial excitation of the second spin type can be determined on the user side. For example, a percentage of the suppression of the second spin type can be adjusted by a corresponding operating element. Alternatively, a qualitative measure of suppression can be set, for example by selecting "weak", "medium" and "strong".

The invention also encompasses a magnetic resonance apparatus having a control computer designed to operate the scanner of the apparatus in order to implement the method according to the invention. The control computer can have a superimposition processor for preparatory calculated superimposition of the excitation pulse sequence and the additional pulse sequence and/or a frequency controller to emit the resulting pulses of the total pulse sequence by controlling the corresponding radio-frequency components of the magnetic resonance scanner. All statements relating to the method according to the invention are applicable to the magnetic resonance apparatus according to the invention, with which the aforementioned advantages also can be achieved.

The invention also encompasses a non-transitory, computer-readable data storage medium encoded with programming instructions that, when the storage medium is loaded into a control computer or (distributively) a computer system of a magnetic resonance apparatus, cause the control computer or computer system to operate the magnetic resonance apparatus in order to implement any or all of the embodiments of the method according to the invention, as described above.

The data carrier can be a CD-ROM.

DESCRIPTION OF THE PREFERRED EMBODIMENTS

The following now describes different exemplary embodiments of the method according to the invention for spins of water-bound protons (hydrogen atoms) as a first spin type and spins of fat-bound protons (hydrogen atoms) as a second spin type. Herein, in the present case, the imaging is primarily intended to relate to the water spins, wherein signals of the fat spins are to be suppressed, although in the present case not completely, but only partially, in order, for example, to obtain an anatomical "context" in the case of orthopedic recordings. This means, the first spin type and the second spin type are each excited, but to different degrees, wherein the first spin type is to be excited to a greater degree than the second spin type.

Figure 1:
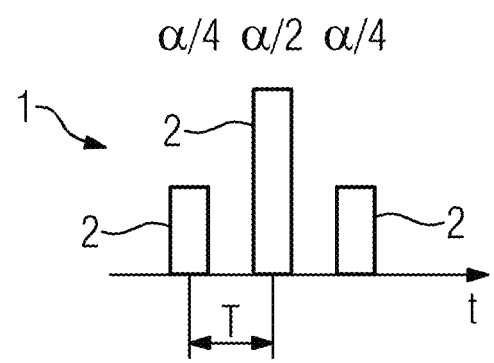
FIG. 1 shows an exemplary excitation pulse sequence.

Here, assumed in each case is water excitation, i.e. a spectrally selective excitation pulse sequence that only relates to water. Such an excitation pulse sequence 1 is depicted schematically in FIG. 1, wherein its individual excitation pulses 2, here only indicated schematically, are embodied as square-wave pulses (with spatial selective excitation as sinc pulses). This is a binomial excitation pulse sequence 1, which in the present case comprises three excitation pulses 2 in chronological sequence with a relative excited flip angle that can be described as binomial coefficients 1-2-1. Since there is to be an overall excitation of the water spins by a flip angle $\alpha$, the first excitation pulse 2 therefore relates to a flip angle of $\alpha/4$, the second excitation pulse 2 to a flip angle of $\alpha/2$ and the third excitation pulse 2 to a flip angle of $\alpha/4$.

As shown, the individual excitation pulses 2 are each spaced apart by a time interval T. This evolution time T is selected such that a relative phase angle of 180°, i.e. $\pi$, develops between the spins of the first spin type and those of the second spin type to be suppressed. When considering the water and fat protons with a field strength of 3 tesla, T is approximately 1.1 ms. For the water spins, the flip angle contributions of the individual excitation pulses 2 are added together to produce a flip angle $\alpha$. However, for the fat spins, the central excitation pulse 2 has the reverse effect so that a flip angle of 0 (i.e. no excitation) results.

Figure 2:
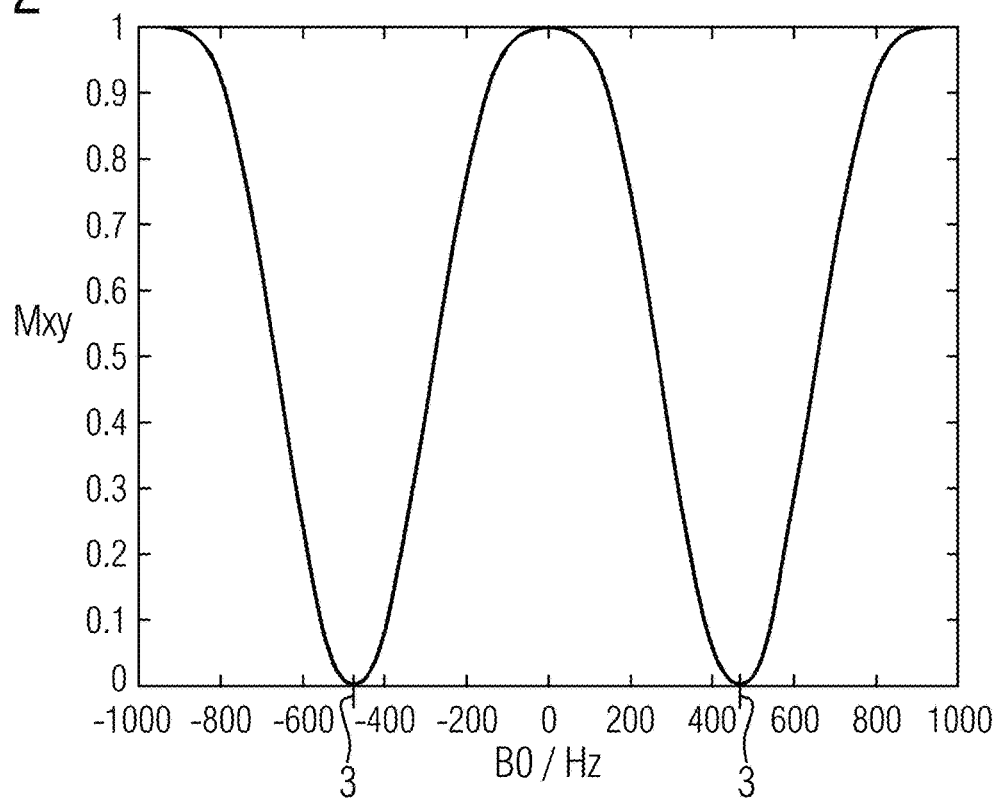
FIG. 2 shows a resulting excitation spectrum as the sole use of the excitation pulse sequence for excitation in a recording volume.

FIG. 2 shows the corresponding excitation spectrum, to be specific the transversal magnetization following the sole use of the excitation pulse sequence 1 versus the spectral shift starting from 0 versus the water spins. As shown, a value of 0 for the spectral shift relative to water spins produces maximum excitation, a value 3 for the spectral shift corresponding to the chemical shift between water-bound protons and fat-bound protons produces a transversal magnetization of 0, i.e. no excitation. In the case of binomial excitation pulse sequences, this excitation pattern is repeated periodically.

Figure 3:
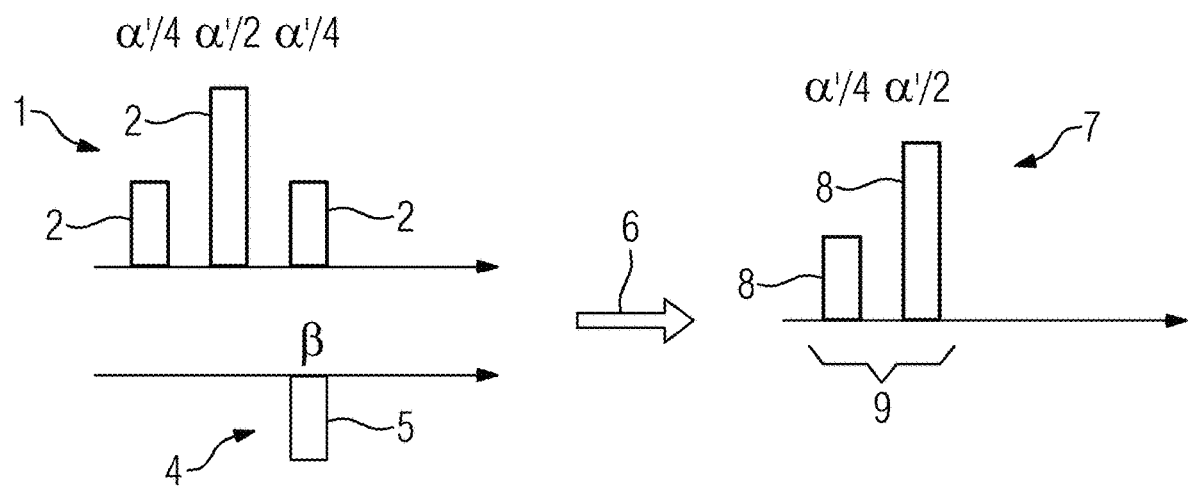
FIG. 3 shows a superimposition of an excitation pulse sequence and an additional pulse sequence and the resulting total pulse sequence.

FIG. 3 explains the basic principle of the method according to the invention using an exemplary embodiment. This on the one hand shows the excitation pulse sequence 1, as already shown in FIG. 1, but in chronological correlation to an additional pulse sequence 4, which in the present case includes one single additional pulse 5, which is chronologically synchronous with the last excitation pulse 2. The additional pulse 5, also a square-wave pulse, relates to both the water spins and the fat spins and would in principle tilt them by a flip angle $\beta$, but which in the present case is selected as $-\alpha/4$ so that the superimposition of the excitation pulse sequence 1 according to the invention that is to be performed now and the additional pulse sequence 4 has the result that the last excitation pulse 2 and the additional pulse 5 exactly cancel the effect of one other, so that they can finally be emitted such that no result pulse at all is emitted at this time.

Therefore, the result of the superimposition according to the arrow 6 is a total pulse sequence 7 now with only two result pulses 8 that are actually to be emitted corresponding to the first two excitation pulses 2. Therefore, as shown, the excitation period in which the total pulse sequence 7 is output can be shortened compared to the duration of the excitation pulse sequence 1, in that, for example, the excitation period 9 is selected.

The result of the use of the total pulse sequence is that the water spins are excited with a flip angle $\alpha=\frac{3}{4}\alpha'$ and the fat spins with a flip angle of $-\alpha'/4$. It is generally possible to state that $\alpha'*(\frac{1}{4}+\frac{1}{2}+\frac{1}{4})-\beta$ must produce the desired flip angle $\alpha$ for the water spins.

Figure 4:
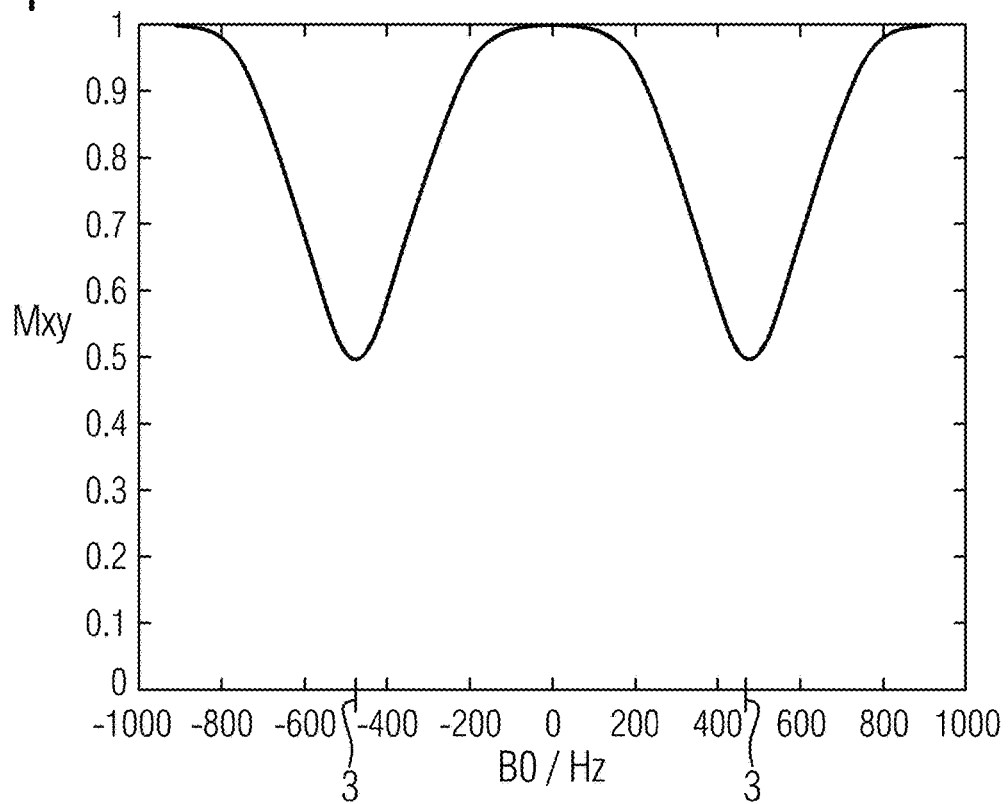
FIG. 4 shows a resulting excitation spectrum on the use of the total pulse sequence shown in FIG. 3.

FIG. 4 shows a resulting excitation spectrum with the use of the total pulse sequence 7. Furthermore, full excitation ($\alpha=90°$, $\sin(\alpha)=1$) is provided for the water spins, i.e. the first spin type, while the second spin type, i.e. the fat spins, are only partially excited ($\beta=-30°$, $\sin(\beta)=0.5$).

As is known in principle, the quality of the spectral separation of pass and stop bands increases as the order of the binomial coefficients increases, for example on the transition from a 1-3-3-1 excitation pulse sequence to a 1-3-3-0 total pulse sequence, a clear separation is achieved. However, at the same time, the number of radio-frequency pulses 8 in the total pulse sequence, and hence the duration of the excitation period, increases so that in practice it is possible to use a suitable optimum for the imaging task.

Figure 5:
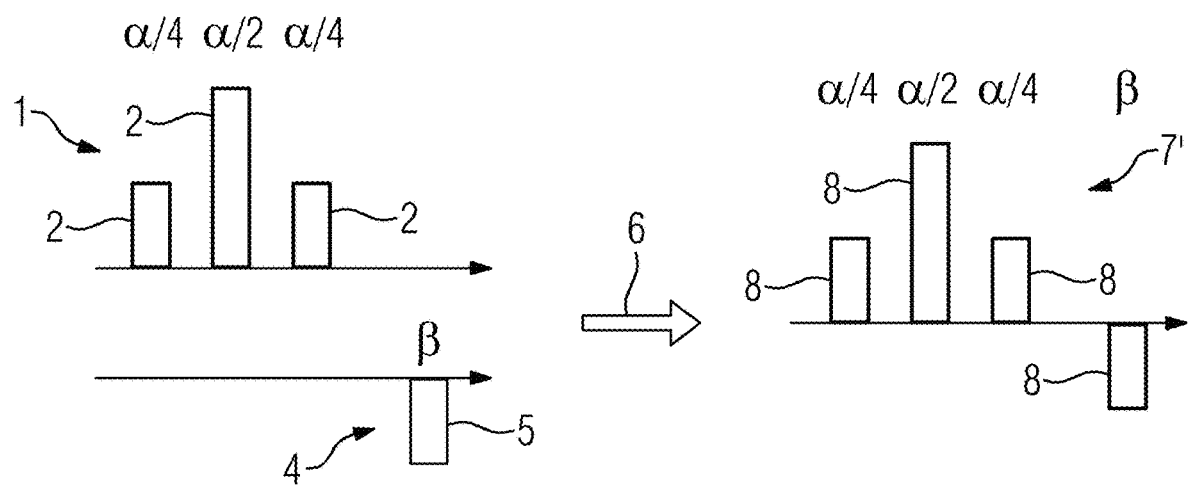
FIG. 5 shows a second exemplary embodiment with an additional pulse sequence following the excitation pulse sequence chronologically.

FIG. 5 shows as a second exemplary embodiment a modification of the embodiment in FIG. 3. Although here the same additional pulse sequence 4 comprising only one signal additional pulse 5 is used, it is chronologically offset, so that in the now resulting total pulse sequence 7' there are still four result pulses. Although this is preferable, therefore generally the additional pulse 5 does not have to be applied synchronously with an excitation pulse 2—it can also be played out beforehand or afterward.

Figure 6:
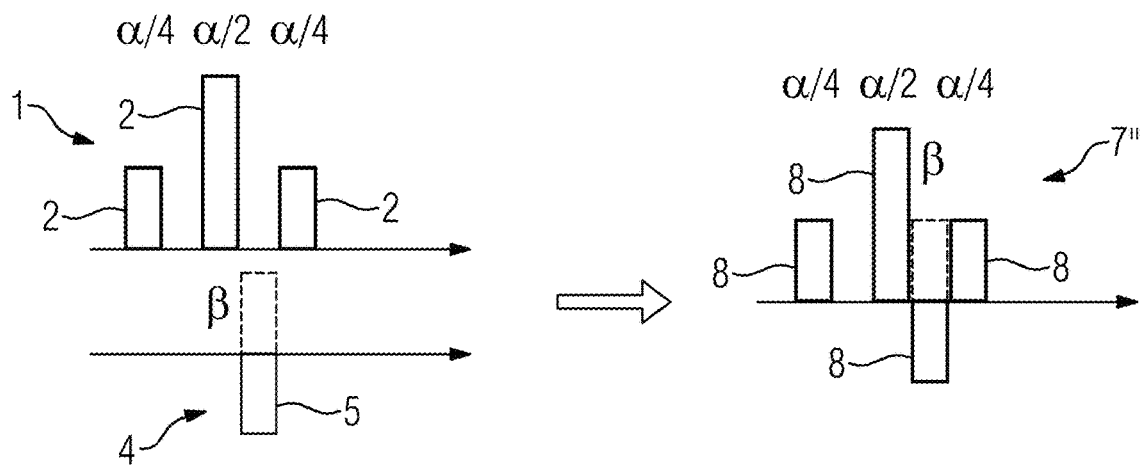
FIG. 6 shows a third exemplary embodiment with non-synchronous superimposition of the pulse sequences.
Figure 7:
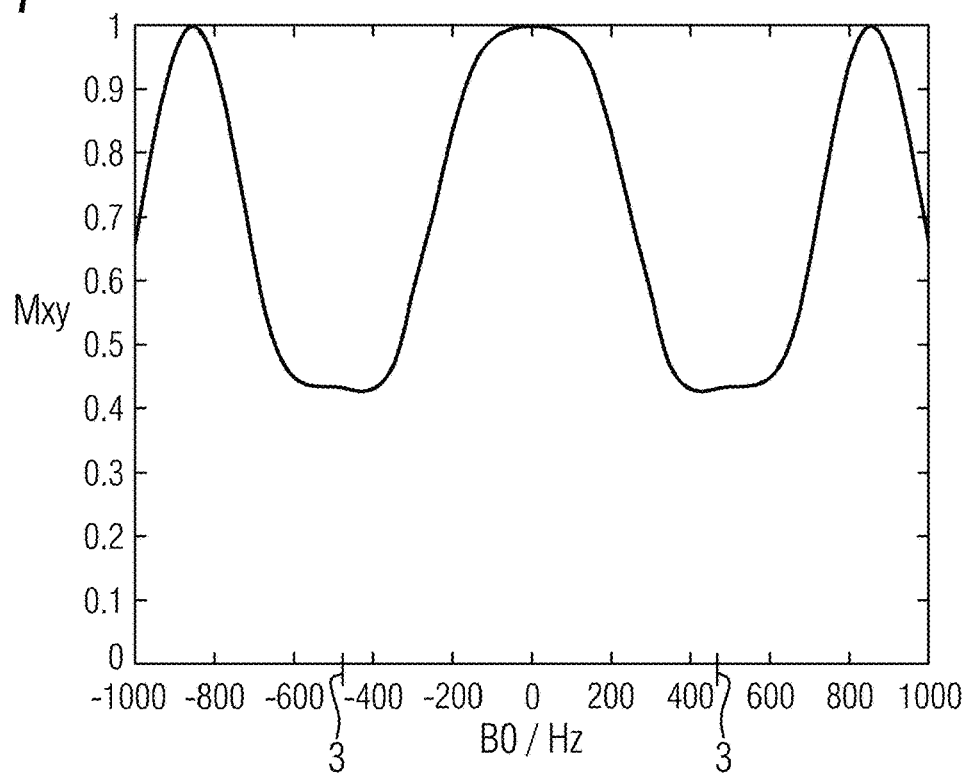
FIG. 7 shows a first resulting frequency spectrum without relative phase shift of an additional pulse with respect to excitation pulses.
Figure 8:
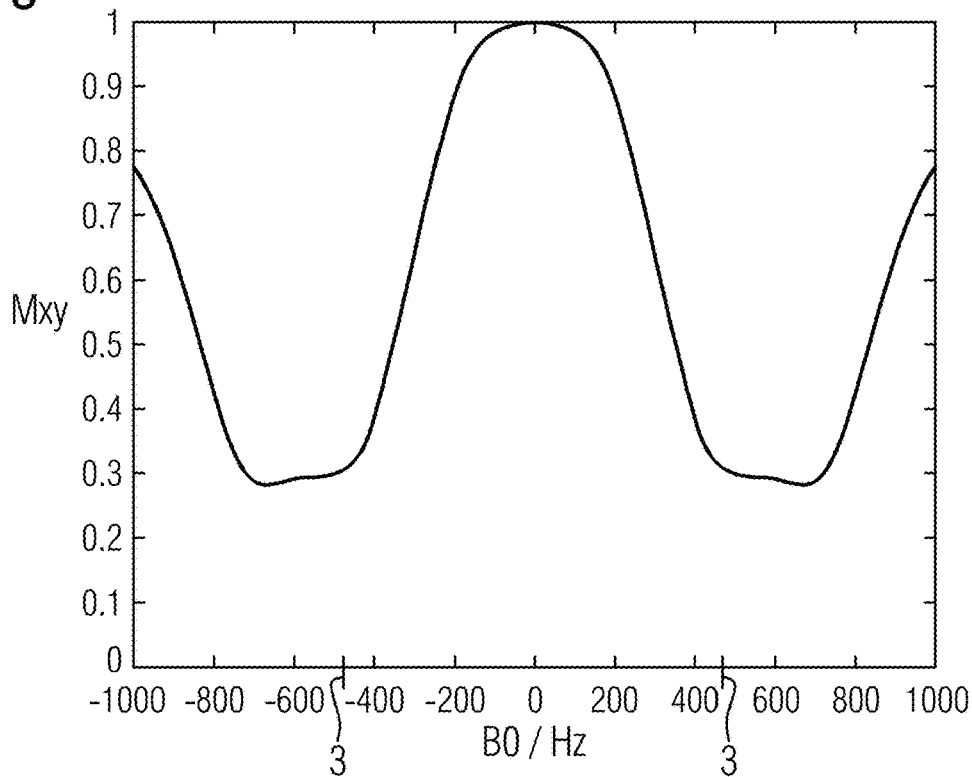
FIG. 8 shows a second resulting excitation spectrum on a relative phase shift of the additional pulse relative to the excitation pulses.

FIG. 6 shows a further modification of the exemplary embodiments in FIG. 3 and FIG. 5, wherein the one additional pulse 5 is here not established before or after the excitation pulse sequence 1 but it is to be played out between the second and the third excitation pulse 2, possibly also with a relative phase angle changed by 180°, as indicated in a dashed line in FIG. 6. The application of the superimposed additional pulse 5 within the spectrally selective excitation pulse sequence 1 does not prolong the overall duration of the excitation. The choice of phase of the superimposed additional pulse 5 already addressed can exert an influence on the shape of the excitation spectrum and the degree of suppression of the second spin type, wherein the excitation spectrum depicted in FIG. 7 is obtained for the relative phase angle 0° and the excitation spectrum depicted in FIG. 8 is obtained with a relative phase angle of 180°.

However, it is preferable, as shown in FIG. 3, to apply the at least one additional pulse 5 synchronously with an excitation pulse 2, which, for example, makes it possible to reduce the duration of the excitation period, as shown in FIG. 3, but on the other hand to enable in a simple way expansion to simultaneously spatially and spectrally selective excitation pulses 2 and additional pulses 5, as will be explained in more detail below.

Figure 9:
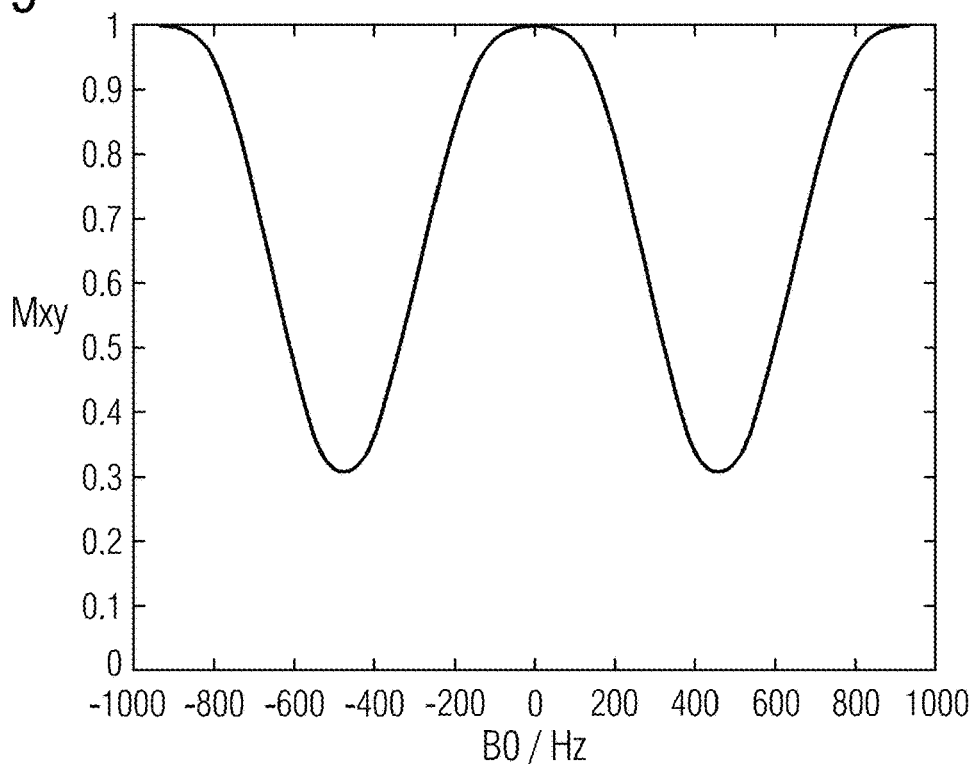
FIG. 9 shows an excitation spectrum on the centric superimposition of an additional pulse sequence with a single additional pulse.

However, first reference is made to the fact that, when used in magnetic resonance sequences sensitive to different echo times, for example in the case of a turbo-spin-echo sequence, centric superimposition is preferable, i.e. superimposition of the additional pulse 5 synchronously with the center excitation pulse 2, so that, for example, with a choice of $\beta=\alpha'/4$, the 1-2-1-excitation pulse sequence 1 would produce a 1-3-1-total pulse sequence, the excitation spectrum of which is depicted in FIG. 9 by way of example.

Figure 10:
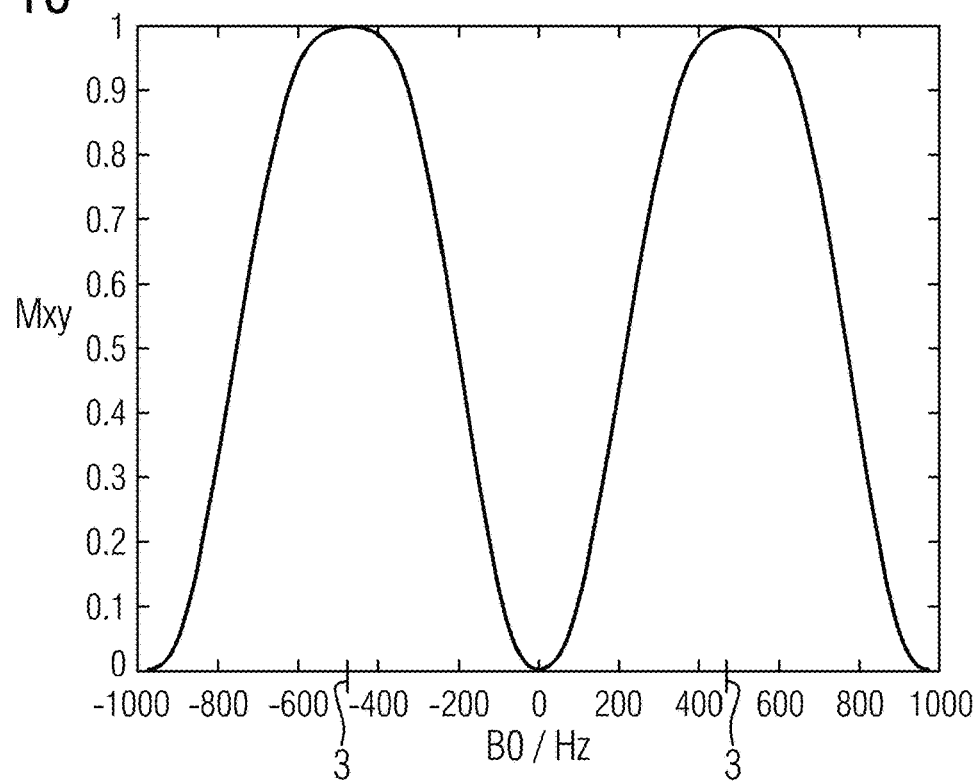
FIG. 10 shows an excitation spectrum of a binomial fat excitation pulse sequence.

In other exemplary embodiments, additional pulse sequences with a plurality of additional pulses 5 are also conceivable, this means that the additional pulse sequence can preferably also be embodied as a binomial pulse sequence, in particular with the same binomial coefficients as the excitation pulse sequence. Therefore, in the above example, a 1-2-1 water excitation pulse sequence can be used as an excitation pulse sequence and a 1-$\underline{2}$-1 fat excitation pulse sequence as an additional pulse sequence. FIG. 10 shows the excitation spectrum of a 1-$\underline{2}$-1 fat excitation pulse sequence, wherein it is evident that, due to the inversion of the second partial pulse (additional pulse), there is complete excitation of the first spin type with the value 3 for the chemical shift but that water spins are not affected at all with a spectral shift of 0 Hz.

Figure 11:
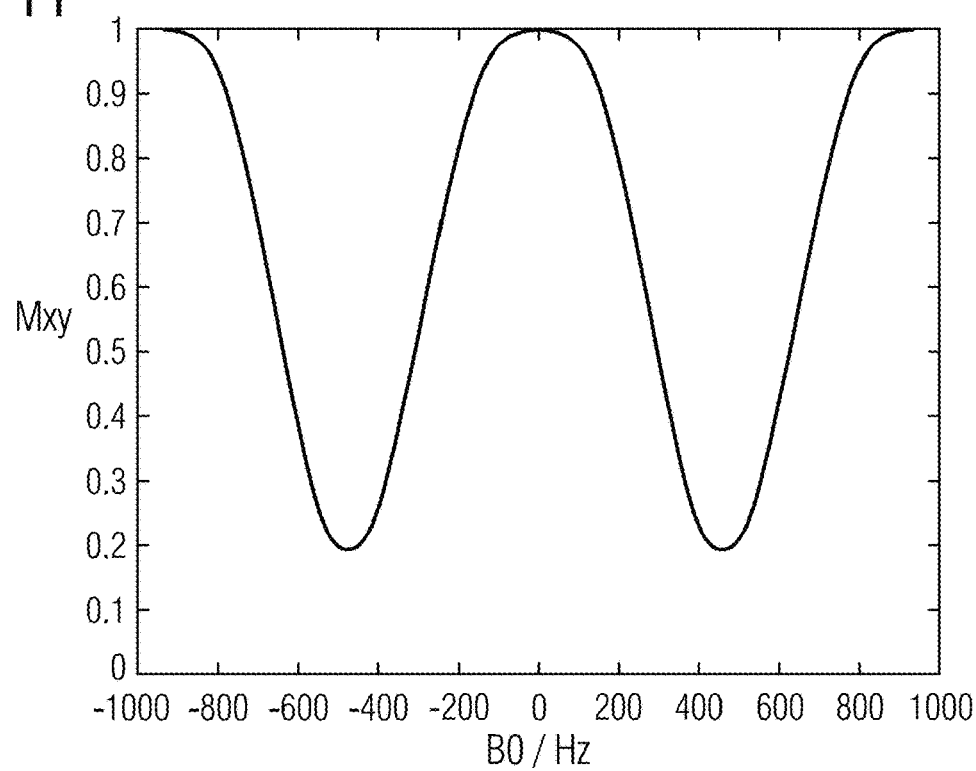
FIG. 11 shows a first excitation spectrum on the superimposition of the fat excitation pulse sequence as an additional pulse sequence via a structurally identical water excitation pulse sequence.

Accordingly, FIG. 11 shows the excitation spectrum with the superimposition of a 1-2-1-$\alpha$-excitation pulse sequence with a 1-$\underline{2}$-1-$\beta$ additional pulse sequence to form a total pulse sequence, wherein here $\beta=\alpha/8$ was selected by way of example, so that a ⅞-18/8-⅞-total pulse sequence occurs as a total pulse sequence. In this embodiment, scaling of the flip angle $\alpha$ is not necessary since the superimposed additional pulses 5 of the additional pulse sequence do not affect the first spin type, i.e. the water spins.

Figure 12:
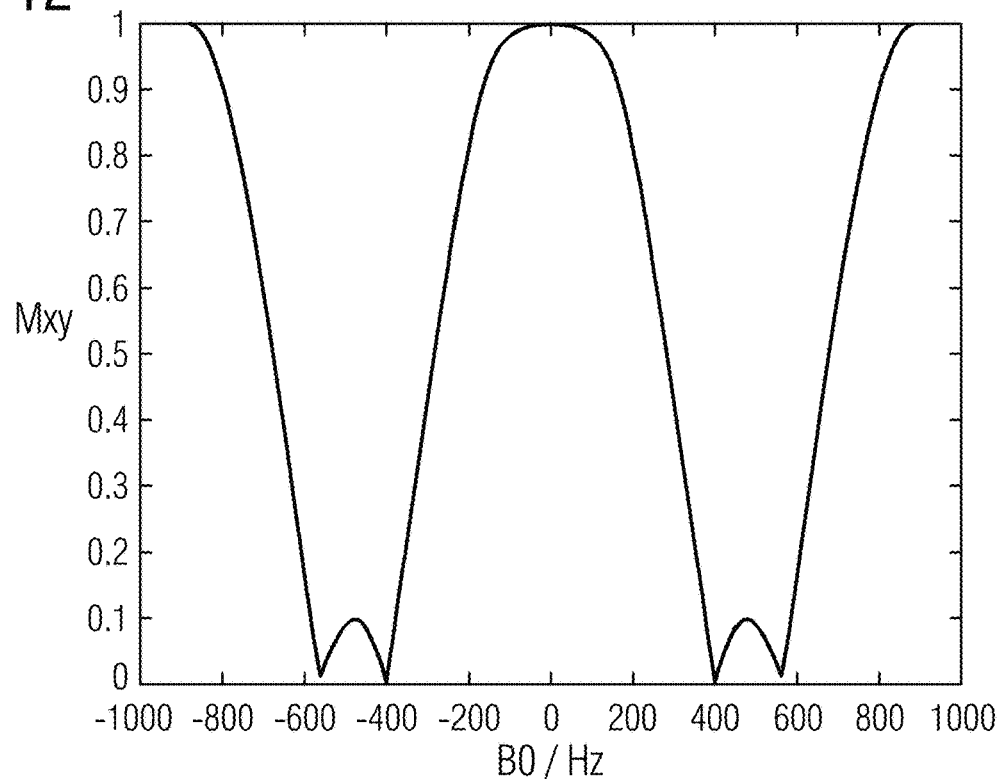
FIG. 12 shows a frequency spectrum on the use of a relative phase shift on the superimposition of the binomial pulse sequences.

Herein, reference is made to the fact that here it is again possible in principle freely to select combined pulse sequences, wherein it should be noted that then the phase of the resulting signal components is different—this is frequently desired due to the reduction in the smoothness of the spectral profiles. However, if, in individual cases, other phase relationships should be useful, other relative phase angles are also conceivable in principle. As an example, the excitation spectrum in FIG. 12 shows an inverted superimposition resulting in a 9/8-16/8-9/8-total pulse sequence, wherein the phase of the fat signal is then the opposite of the phase of the water signal. The figures show the amount of the transversal magnetization.

The procedure according to the invention can preferably be used jointly with dynamic adjustment, wherein then the choice of corresponding pulse sequences and the use of slice-selection gradient pulse sequences also enables the use of spatially selective excitation pulses 2 and additional pulses 5. Herein, as also indicated in FIGS. 13 to 15, sinc pulses are used for example for the excitation pulses 2 and the additional pulses 5.

Figure 13:
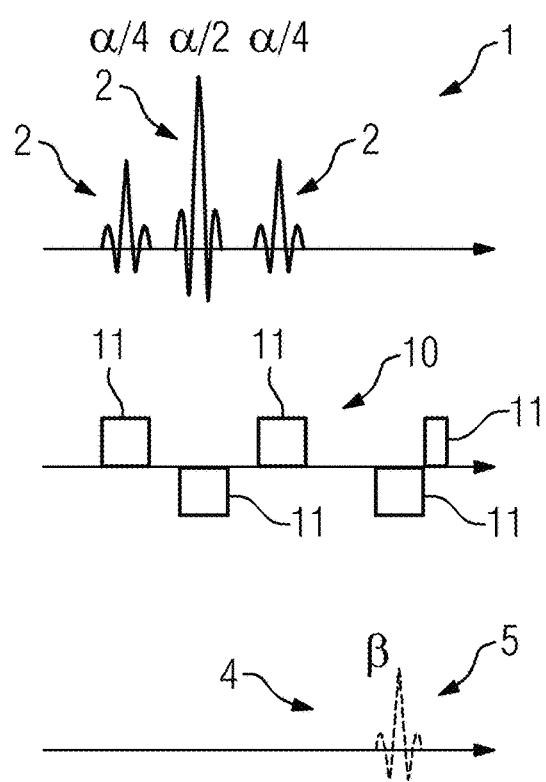
FIG. 13 shows a first exemplary embodiment with spatially selective pulse sequences.

FIG. 13 shows a first exemplary embodiment with spatially selective excitation pulses 2 and spatially selective additional pulses 5. Herein, there the additional pulse 5 is output after the excitation pulse sequence 1, wherein in the gradient pulse sequence 10 a special slice selection gradient pulse 11 is assigned to the output period of the additional pulse 5. Herein, the last gradient pulse 11 of the gradient pulse sequence 10 is used for rephasing. As shown, alternating slice selection gradients are used.

Figure 14:
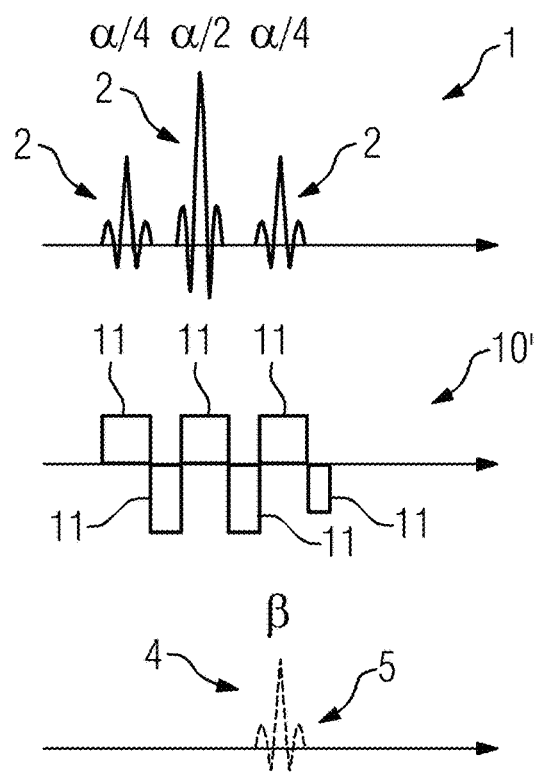
FIG. 14 shows a second exemplary embodiment with spatially selective pulse sequences.

FIG. 14 shows a second exemplary embodiment with spatially selective excitation pulses 2 and a spatially selective additional pulse 5, wherein in this case the additional pulse 5 is applied synchronously with the last excitation pulse 2 and therefore also uses the corresponding gradient pulse 11 of the gradient pulse sequence 10', which here uses flyback slice selection gradients.

Figure 15:
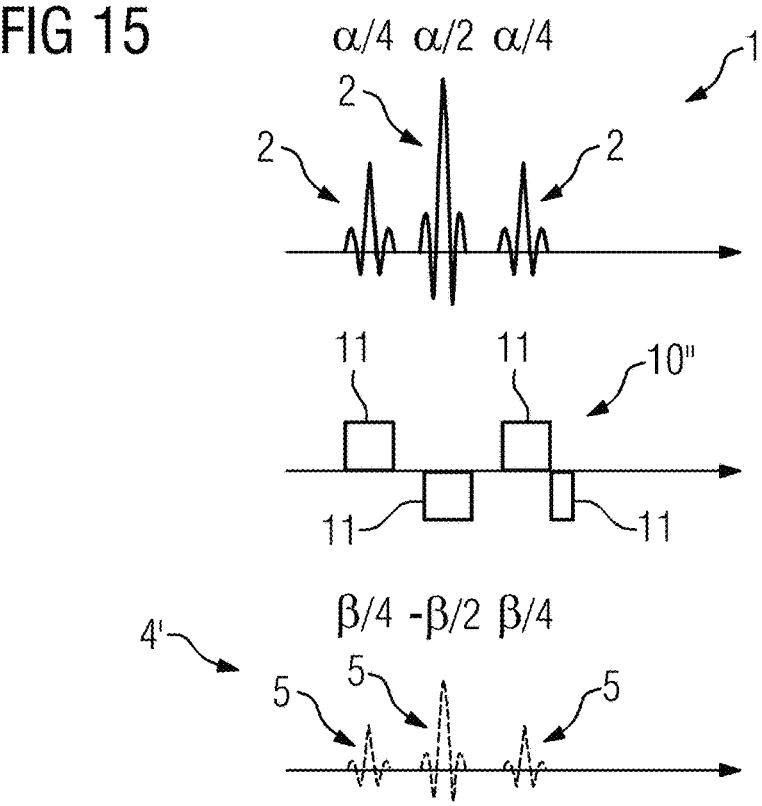
FIG. 15 shows a third exemplary embodiment with spatially selective pulse sequences.

Finally, FIG. 15 shows a third exemplary embodiment with spatially selective excitation pulses 2 and additional pulses 5, wherein here the additional pulse sequence 4' is embodied as a 1-$\underline{2}$-1-binomial pulse sequence, such as was already discussed with respect to FIGS. 10, 11 and 12. The excitation pulses 2 and the additional pulses 5 are superimposed synchronously so that they (or the resulting result pulses 8) can use the corresponding gradient pulses 11 of the gradient pulse sequence 10".

In the case of a recording for magnetic resonance data in a number of recording volumes, in chronological succession, here dynamic adjustment is used in parallel and this is expressed in the adjustment of the shim parameters of a shim device of the magnetic resonance device used in exactly the same way as in the adjustment of pulse parameters. As an example, the center frequency can be adjusted. This exploits the fact that the spatially spectral excitation techniques used here also act locally and hence benefit significantly from the local optimization of the shims and enable the simple implementation of the adjustment of pulse parameters.

Figure 16:
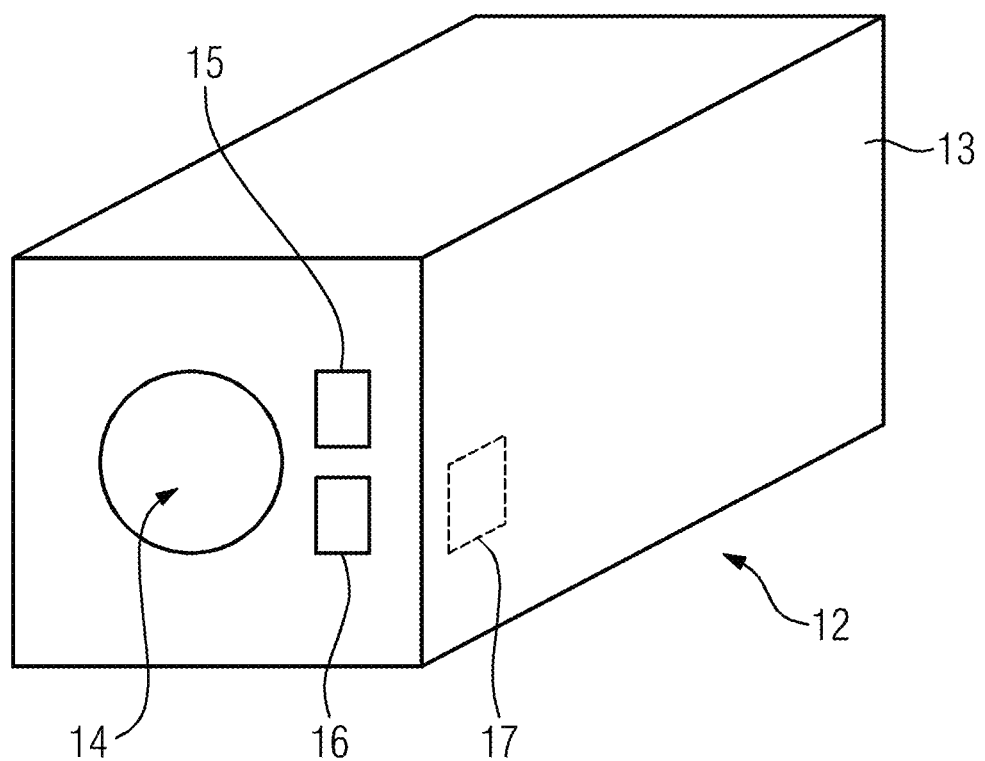
FIG. 16 schematically illustrates a magnetic resonance apparatus according to the invention.

FIG. 16 schematically shows a magnetic resonance apparatus 12 according to the invention. As is known in principle, this includes a scanner 13 that has a basic field magnet, having a patient receiving receptacle 14 for a patient to be examined. The scanner 13 also has a shim device 15 and at least one transmit coil 16, via which the excitation pulses 2/additional pulses 5 or result pulses 8 are radiated. The operation of the magnetic resonance scanner 13 is controlled by a control computer 17 designed to carry out the method according to the invention. This preferably has a superimposition processor in which the total pulse sequence is determined by calculation. A sequence controller of the control computer 17, in particular a transmitting sub-unit of this sequence controller, controls the corresponding transmit components for emitting the result pulses 8, which can then be radiated by at least one transmit coil. The transmit coil 16 can also be a local coil assembly. The control computer 17 can also have a dynamic adjustment processor in order to be able to carry out the described dynamic adjustment.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for exciting two different nuclear spin types respectively with different degrees of excitation, said two different nuclear spin types each having a Larmor frequency, said method comprising:
    in a computer, defining an excitation pulse sequence with at least two consecutive excitation pulses having defined time intervals for exclusively exciting a first of said two spin types;
    in said computer, defining an additional pulse sequence with at least one additional pulse that acts at least on a second of said two spin types;
    in said computer, producing a total pulse sequence having an excitation period in which said excitation pulse sequence and said additional pulse sequence are superimposed;
    from said computer, operating a magnetic resonance (MR) data acquisition scanner by emitting control signals to said MR data acquisition scanner that operate the MR data acquisition scanner according to said total pulse sequence, with the respective Larmor frequencies of said first of said two different spin types and said second of said two different spin types being shifted relative to each other during acquisition of MR data with said total pulse sequence, and with said first of said two different spin types and said second of said two different spin types being excited to respectively different degrees by said superimposed excitation pulse sequence and said additional pulse sequence; and
    in said computer, compiling the MR data acquired with said total pulse sequence in a memory as a data file, and making the data file available from the computer in electronic form.

2. A method as claimed in claim 1 comprising generating said total pulse sequence with said excitation period wherein said excitation pulse sequence and said additional pulse sequence are only partially superimposed.

3. A method as claimed in claim 2 comprising generating said total pulse sequence wherein said at least one additional pulse is radiated in said MR data acquisition scanner after an end of said excitation pulse sequence.

4. A method as claimed in claim 2 wherein said at least one additional pulse is superimposed synchronously with an excitation pulse of the excitation pulse sequence.

5. A method as claimed in claim 2 wherein said additional pulse sequence comprises an additional pulse that compensates an excitation pulse that is radiated at a start or at an end of said excitation pulse sequence, and wherein a duration of said excitation period of said total pulse sequence is set in said computer to be shorter than a duration of said excitation pulse sequence.

6. A method as claimed in claim 1 wherein said additional pulse sequence comprises at least two consecutive additional pulses with defined time intervals for exclusive excitation of said second of said two different spin types, so that a flip angle produced by said additional pulse sequence is smaller than a flip angle produced by said excitation pulse sequence.

7. A method as claimed in claim 1 comprising, in said total pulse sequence, operating said MR data acquisition scanner to radiate said at least one additional pulse of said additional pulse sequence with a relative phase with respect to the excitation pulses of said excitation pulse sequence.

8. A method as claimed in claim 1 comprising producing said total pulse sequence in said computer so as to also comprise a gradient pulse sequence that spatially selects a portion of an examination subject in which said two different spin types are excited.

9. A method as claimed in claim 7 comprising producing said total pulse sequence with said two consecutive excitation pulses of said excitation pulse sequence, and said at least one additional pulse of said additional pulse sequence, are pulses selected from the group consisting of sinc pulses, Gaussian pulses, and sinusoidal half-waves.

10. A method as claimed in claim 7 comprising producing said total pulse sequence with said spatially selective gradient pulse sequence being selected from the group consisting of alternating slice selection gradients, and a gradient pulse sequence comprising a flyback technique.

11. A method as claimed in claim 8 comprising, from said computer, operating said MR data acquisition scanner with said total pulse sequence with a dynamic spatially selective adjustment of at least one pulse parameter of said at least two consecutive pulses of said excitation pulse sequence or said at least one additional pulse of said additional pulse sequence.

12. A method as claimed in claim 8 comprising operating said MR data acquisition scanner with said total pulse sequence with dynamic spatially selective adjustment of at least one shim parameter of a shim device that shims a basic magnetic field in said MR data acquisition scanner.

13. A method as claimed in claim 1 comprising receiving a manual entry into said computer that sets the relative degrees of excitation of said first of said two spin types and said second of said two spin types.

14. A method as claimed in claim 1 comprising operating said MR data acquisition scanner with said total pulse sequence using a binomial pulse sequence as at least one of said excitation pulse sequence or said additional pulse sequence.

15. A method as claimed in claim 1 wherein said first of said two spin types is water-bound protons and wherein a second of said two different spin types is fat-bound protons.

16. A method as claimed in claim 1 comprising producing said total pulse sequence as a turbo-spin-echo sequence.

17. A magnetic resonance (MR) apparatus comprising:
    an MR data acquisition scanner;
    a computer configured to define an excitation pulse sequence with at least two consecutive excitation pulses having defined time intervals for exclusively exciting a first of said two spin types;
    said computer being configured to define an additional pulse sequence with at least one additional pulse that acts at least on a second of said two spin types;
    said computer being configured to produce a total pulse sequence having an excitation period in which said excitation pulse sequence and said additional pulse sequence are superimposed;
    said computer being configured to operate a magnetic resonance (MR) data acquisition scanner by emitting control signals to said MR data acquisition scanner that operate the MR data acquisition scanner according to said total pulse sequence, with the respective Larmor frequencies of said first of said two different spin types and said second of said two different spin types being shifted relative to each other during acquisition of MR data with said total pulse sequence, and with said first of said two different spin types and said second of said two different spin types being excited to respectively different degrees by said superimposed excitation pulse sequence and said additional pulse sequence; and
    said computer being configured to compile the MR data acquired with said total pulse sequence in a memory as a data file, and making the data file available from the computer in electronic form.

18. A non-transitory, computer-readable data storage medium encoded with programming instructions, said storage medium being loaded into a computer system of a magnetic resonance (MR) apparatus comprising an MR data acquisition scanner, and said programming instructions causing said computer system to:
- define an excitation pulse sequence with at least two consecutive excitation pulses having defined time intervals for exclusively exciting a first of said two spin types;
- define an additional pulse sequence with at least one additional pulse that acts at least on a second of said two spin types;
- produce a total pulse sequence having an excitation period in which said excitation pulse sequence and said additional pulse sequence are superimposed;
- operate a magnetic resonance (MR) data acquisition scanner by emitting control signals to said MR data acquisition scanner that operate the MR data acquisition scanner according to said total pulse sequence, with the respective Larmor frequencies of said first of said two different spin types and said second of said two different spin types being shifted relative to each other during acquisition of MR data with said total pulse sequence, and with said first of said two different spin types and said second of said two different spin types being excited to respectively different degrees by said superimposed excitation pulse sequence and said additional pulse sequence; and
- compile the MR data acquired with said total pulse sequence in a memory as a data file, and make the data file available from the computer in electronic form.

* * * * *